United States Patent
Mitsuhashi

(10) Patent No.: US 8,574,151 B2
(45) Date of Patent: Nov. 5, 2013

(54) IN-VIVO INFORMATION ACQUIRING SYSTEM AND BODY-INSERTABLE APPARATUS

(75) Inventor: Kei Mitsuhashi, Nishitokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1371 days.

(21) Appl. No.: 12/327,350

(22) Filed: Dec. 3, 2008

(65) Prior Publication Data

US 2009/0149704 A1    Jun. 11, 2009

(30) Foreign Application Priority Data

Dec. 5, 2007 (JP) ................................ 2007-314621

(51) Int. Cl.
*A61B 1/00* (2006.01)
*A61B 1/06* (2006.01)

(52) U.S. Cl.
USPC .......... 600/118; 600/103; 600/117; 600/160; 600/178; 348/65; 348/69

(58) Field of Classification Search
USPC ........... 600/103, 117, 118, 160, 178; 348/65, 348/69; 396/17; 386/201
See application file for complete search history.

(56) References Cited

U.S. PATENT DOCUMENTS

| | | | |
|---|---|---|---|
| 6,064,795 A * | 5/2000 | Uchide | 386/330 |
| 6,215,517 B1 | 4/2001 | Takahashi et al. | |
| 6,904,308 B2 | 6/2005 | Frisch et al. | |
| 7,022,067 B2 * | 4/2006 | Glukhovsky et al. | 600/109 |
| 2002/0103417 A1 * | 8/2002 | Gazdzinski | 600/109 |
| 2002/0196335 A1 | 12/2002 | Ozawa | |
| 2007/0070193 A1 * | 3/2007 | Abe | 348/65 |
| 2007/0083083 A1 | 4/2007 | Mori et al. | |
| 2008/0068453 A1 | 3/2008 | Mori et al. | |
| 2008/0100698 A1 | 5/2008 | Mori et al. | |

FOREIGN PATENT DOCUMENTS

| | | |
|---|---|---|
| CN | 1960668 A | 5/2007 |
| CN | 101057490 A | 10/2007 |
| EP | 1 679 029 A1 | 7/2006 |
| JP | 10-286231 | 10/1998 |

(Continued)

OTHER PUBLICATIONS

English Language Abstract of Japanese Patent Application No. JP 2006-140642 published Jun. 1, 2006.

(Continued)

*Primary Examiner* — Philip R Smith
*Assistant Examiner* — Rynae Boler
(74) *Attorney, Agent, or Firm* — Scully, Scott, Murphy & Presser, P.C.

(57) ABSTRACT

A body-insertable apparatus includes an imaging unit that captures an in-vivo image of a subject; a signal processing unit that writes the in-vivo image in a memory, reads the in-vivo image from the memory on a pixel basis and converts the in-vivo image to serial information to transfer the serial information; and a rate converter that converts a transfer processing rate to a rate higher than a writing processing rate. The transfer processing rate is at which the signal processing unit reads the in-vivo image from the memory and converts the in-vivo image to the serial information to transfer the serial information. The writing processing rate is at which the signal processing unit writes the in-vivo image in the memory. The apparatus also includes a transmitting unit that wirelessly transmits the serial information transferred from the signal processing unit at a transmission rate corresponding to the transfer processing rate.

6 Claims, 7 Drawing Sheets

(56) References Cited

FOREIGN PATENT DOCUMENTS

| | | |
|---|---|---|
| JP | 2001-231186 | 8/2001 |
| JP | 2002-44682 | 2/2002 |
| JP | 2003-19111 | 1/2003 |
| JP | 2003-126030 | 5/2003 |
| JP | 2003-135392 | 5/2003 |
| JP | 2004-033451 | 2/2004 |
| JP | 2005-020755 | 1/2005 |
| JP | 2005-319098 | 11/2005 |
| JP | 2005-334080 | 12/2005 |
| JP | 2006-140642 | 6/2006 |
| JP | 2006-250824 | 9/2006 |
| JP | 2006-304867 | 11/2006 |
| JP | 2007-276191 | 10/2007 |
| WO | WO 03/010967 A1 | 2/2003 |
| WO | WO 2005/084521 A1 | 9/2005 |
| WO | WO 2005/115217 A1 | 12/2005 |

OTHER PUBLICATIONS

English Language Abstract of Japanese Patent Application No. JP 2003-135392 published Mar. 13, 2003.

English Language Abstract of Japanese Patent Application No. JP 10-286231 published Oct. 27, 1998.

English Language Abstract of Japanese Patent Application No. JP 2005-319098 published Nov. 17, 2005.

* cited by examiner

IN-VIVO INFORMATION ACQUIRING SYSTEM AND BODY-INSERTABLE APPARATUS

CROSS-REFERENCE TO RELATED APPLICATIONS

This application is based upon and claims the benefit of priority from Japanese Patent Application No. 2007-314621, filed Dec. 5, 2007, the entire contents of which are incorporated herein by reference.

BACKGROUND OF THE INVENTION

1. Field of the Invention

The present invention relates to a body-insertable apparatus that acquires an in-vivo image and an in-vivo information acquiring system.

2. Description of the Related Art

Recently, in the field of endoscopes, swallowable capsule endoscopes have been developed. A swallowable capsule endoscope has an imaging function such as an image sensor and a wireless function. After being swallowed from the mouth of a patient and until being naturally discharged from the body of the patient, the capsule endoscope sequentially captures in-vivo images while moving through the organs including the esophagus, the stomach, and the small intestine depending on peristalsis (see, for example, Japanese Patent Application Laid-open Nos. 2003-19111 and 2001-231186). While the capsule endoscope moves through the body cavities, the image data acquired by the capsule endoscope is wirelessly transmitted to the outside sequentially and stored in a memory provided to an external receiving apparatus. A doctor or a nurse displays the image data stored in the memory on a display to diagnose the patient.

To further facilitate finding of a lesion during a diagnosis, there is a demand for such capsule endoscopes to capture more images than those captured by a conventional capsule endoscope by increasing the frame rate. To satisfy the demand, there has been proposed a capsule endoscope in which the amount of data to be transmitted is reduced by compressing the image data, so that the time required for transmitting the image data is shortened and the frame rate increases (for example, see International Publication No. 2003/010967).

SUMMARY OF THE INVENTION

A body-insertable apparatus according to an aspect of the present invention includes an imaging unit that captures an in-vivo image of a subject; a signal processing unit that writes the in-vivo image in a memory, reads the in-vivo image from the memory on a pixel basis and converts the in-vivo image to serial information to transfer the serial information; and a rate converter that converts a transfer processing rate to a rate higher than a writing processing rate. The transfer processing rate is at which the signal processing unit reads the in-vivo image from the memory and converts the in-vivo image to the serial information to transfer the serial information. The writing processing rate is at which the signal processing unit writes the in-vivo image in the memory. The apparatus also includes a transmitting unit that wirelessly transmits the serial information transferred from the signal processing unit at a transmission rate corresponding to the transfer processing rate.

An in-vivo information acquiring system according to another aspect of the present invention includes the body-insertable apparatus according to the invention; and a receiving apparatus that receives the wireless signal received from the body-insertable apparatus.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention are explained in detail below with reference to the accompanying drawings.

Figure 1:
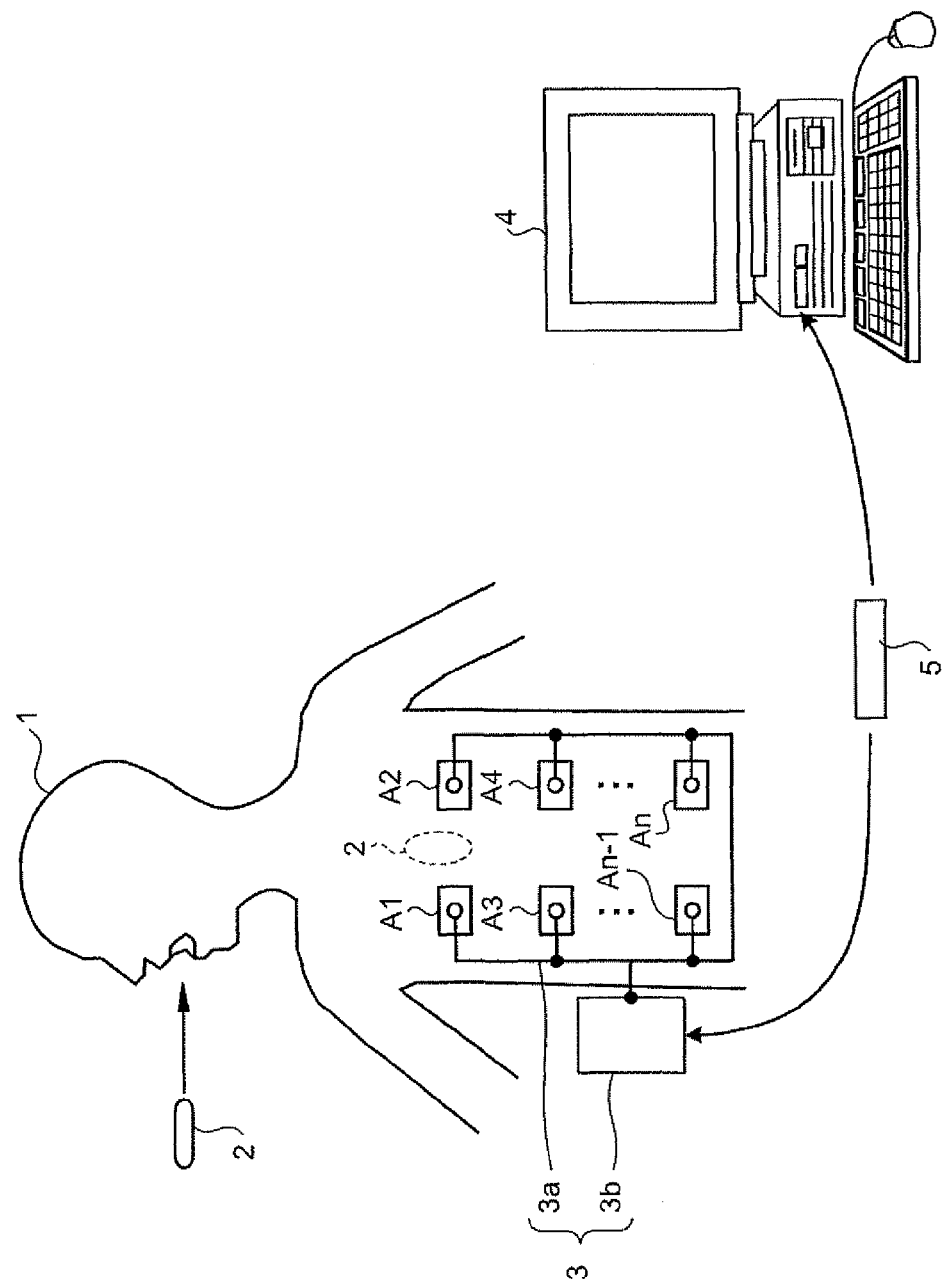
FIG. 1 is a schematic diagram of a configuration of an in-vivo information acquiring system according to an embodiment of the preset invention.

A wireless in-vivo information acquiring system according to an embodiment is explained below. FIG. 1 is a schematic diagram of a configuration of the in-vivo information acquiring system. The in-vivo information acquiring system includes a single-lens capsule endoscope 2 as an example of a body-insertable apparatus. As shown in FIG. 1, the in-vivo information acquiring system includes the capsule endoscope 2 that is introduced into a subject 1, captures an in-vivo image, and wirelessly transmits image data about the in-vivo image as, for example, an image signal to a receiving apparatus 3; the receiving apparatus 3 that receives the image data wirelessly transmitted from the capsule endoscope 2; a processing apparatus 4 that displays the in-vivo image based on the image signal received by the receiving apparatus 3; and a portable recording medium 5 used for data exchange between the receiving apparatus 3 and the processing apparatus 4.

The receiving apparatus 3 includes a wireless unit 3a including a plurality of receiving antennas A1 to An to be attached to the body surface of the subject 1, and a receiving main unit 3b that processes a wireless signal received via the receiving antennas A1 to An. The wireless unit 3a and the receiving main unit 3b are connectable via, for example, a connector. The receiving antennas A1 to An are provided to, for example, a jacket to be worn by the subject 1. In this case, by wearing the jacket, the subject 1 is attached with the receiving antennas A1 to An. In addition, the receiving antennas A1 to An can be configured to be detachable from the jacket.

The processing apparatus 4 processes the in-vivo image captured by the capsule endoscope 2, and displays the processed in-vivo image. The processing apparatus 4 is configured as, for example, a workstation that displays an image based on data received from the portable recording medium 5.

Specifically, the processing apparatus 4 can be configured to directly display an image on a cathode ray tube (CRT) display or a liquid crystal display (LCD) or can be configured as, for example, a printer that outputs the image to other media.

The portable recording medium 5 is, for example, a memory such as the CompactFlash®. The portable recording medium 5 is attachable to the receiving main unit 3b and the processing apparatus 4, and outputs or stores information while being inserted to the receiving main unit 3b or the processing apparatus 4. Specifically, while the capsule endoscope 2 moves thorough the body cavities of the subject 1, the portable recording medium 5 is inserted into the receiving main unit 3b and the data transmitted from the capsule endoscope 2 is stored in the portable recording medium 5. After the capsule endoscope 2 is excreted from the subject 1, i.e., after the capsule endoscope 2 finishes capturing in-vivo images, the portable recording medium 5 is detached from the receiving main unit 3b and inserted into the processing apparatus 4 and the processing apparatus 4 reads the data from the portable recording medium 5. Because the portable recording medium 5 is used to exchange data between the receiving main unit 3b and the processing apparatus 4, the subject 1 can move freely while in-vivo images are captured. The use of the portable recording medium 5 also shortens the time necessary for exchanging data between the receiving main unit 3b and the processing apparatus 4. Instead of the portable recording medium 5, a storage device to be wired or wirelessly connected to the processing apparatus 4 can be installed in the receiving main unit 3b, which allows data exchange between the receiving main unit 3b and the processing apparatus 4.

Figure 2:
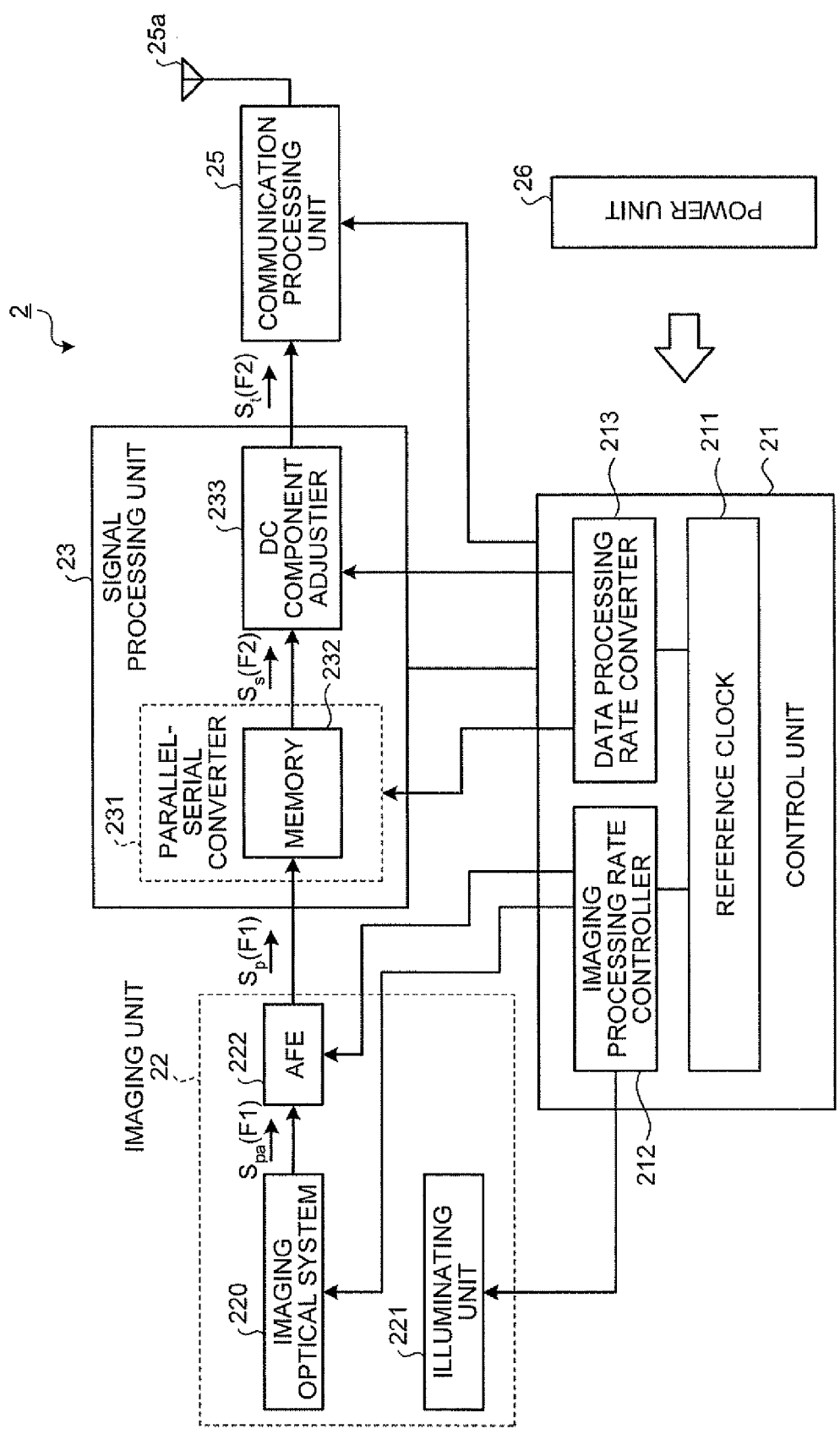
FIG. 2 is a block diagram of a configuration of a capsule endoscope shown in FIG. 1.

A configuration of the capsule endoscope 2 is explained in detail below. FIG. 2 is a block diagram of a configuration of the capsule endoscope 2.

As shown in FIG. 2, the capsule endoscope 2 includes a control unit 21 that controls driving of each unit of the capsule endoscope 2 and controls input of signals to each unit of the capsule endoscope 2 and output of signals from each unit of the capsule endoscope 2, an imaging unit 22, a signal processing unit 23, a communication processing unit 25, and a power unit 26 that supplies drive power to each unit of the capsule endoscope 2.

The imaging unit 22 captures in-vivo images that are images of the body cavities of the subject 1. The imaging unit 22 includes an imaging optical system 220, an illuminating unit 221, and an analog front end (AWE) 222. The imaging optical system 220 includes an imaging device such as a charge coupled device (CCD) or a complementary metal oxide semiconductor (CMOS), and an optical system such as a lens that focuses a light reflected from a site whose image is to be captured on the imaging device. In the imaging optical system 220, the light reflected from the site whose image is to be captured is received and the light is photoelectrically converted, so that image data is obtained on a frame basis. The illuminating unit 221 includes a light emitting diode (LED) that illuminates the site whose image is to be captured by the imaging optical system 220. The AFE 222 reads image data $S_{pa}$ (analog electric signal) acquired by the imaging optical system 220, performs automatic gain control (AGC) processing and A/D conversion processing on the image data $S_{pa}$, and outputs parallel image data $S_p$ (digital signal) to the signal processing unit 23. The imaging unit 22 can be a plurality of imaging units.

The image signal processing unit 23 processes the in-vivo image captured by the imaging unit 22. The signal processing unit 23 includes a parallel-serial converter 231 including a memory 232, and a DC component adjuster 233 (for example, 8-10 bit converter). The signal processing unit 23 can exclude the DC component adjuster 233. FIG. 2 represents only the components relating to conversion of image data as the components of the signal processing unit 23.

The memory 232 temporarily stores image data about the in-vivo image received from the AFE 222. The parallel-serial converter 231 writes the image data $S_p$ received from the AFE 222 in the memory 232 and temporarily stores the image data $S_p$ in the memory 232. The parallel-serial converter 231 reads the image data from the memory 232 on a pixel basis, converts the image data to 8-bit serial data $S_s$, and transfers the serial data $S_s$ (8-bit data) to the DC component adjuster 233. The DC component adjuster 233 converts the serial data $S_s$ (8-bit data) to 10-bit data image data $S_t$ to adjust a DC component, and transfers the image data $S_t$ (10-bit data) to the communication processing unit 25.

The communication processing unit 25 includes an antenna 25a. The antenna 25a is, for example, a coil antenna and used for exchanging wireless signals with external antennas. The communication processing unit 25 modulates each signal to be transmitted to the receiving apparatus 3 and demodulates a wireless signal received via the antenna 25a.

The capsule endoscope 2 converts a transfer processing rate at which the signal processing unit 23 reads the in-vivo image from the memory 232, converts the in-vivo image into serial data S5, and transfers the serial data $S_s$ to a rate higher than a writing processing rate at which the signal processing unit 23 writes the in-vivo image captured by the imaging unit 22 in the memory 232. This shortens the time required for wirelessly transmitting the in-vivo image to the outside after the in-vivo image is captured, so that the imaging unit 22 can capture in-vivo images at short intervals.

Specifically, the control unit 21 includes an imaging processing rate controller 212 that controls an imaging processing rate at which the imaging unit 22 captures in-vivo images by processing a clock of a reference clock 211, and a data processing rate converter 213 that controls a processing rate of the parallel-serial converter 231 and the DC component adjuster 233 by processing a clock of the reference clock 211.

The data processing rate converter 213 converts a transfer processing rate F2, at which the signal processing unit 23 reads the image data $S_p$ about the in-vivo image captured by the imaging unit 22 from the memory 232 on a pixel basis, converts the image data to the serial data $S_s$, and transfers the serial data $S_s$, to a rate higher than a writing processing rate F1 at which the signal processing unit 23 writes the image data $S_p$ in the memory 232. The data processing rate converter 213 increases the transfer processing rate by increasing a clock rate corresponding to the transfer processing rate and to be supplied to the signal processing unit 23 to a clock rate higher than a clock rate to be supplied for the imaging processing performed by the imaging unit 22 and higher than a clock rate to be supplied for the processing for writing the image data $S_p$ in the memory 232. The data processing rate converter 213 includes a frequency converting circuit configured to convert a clock frequency of the reference clock 211.

Figure 3:
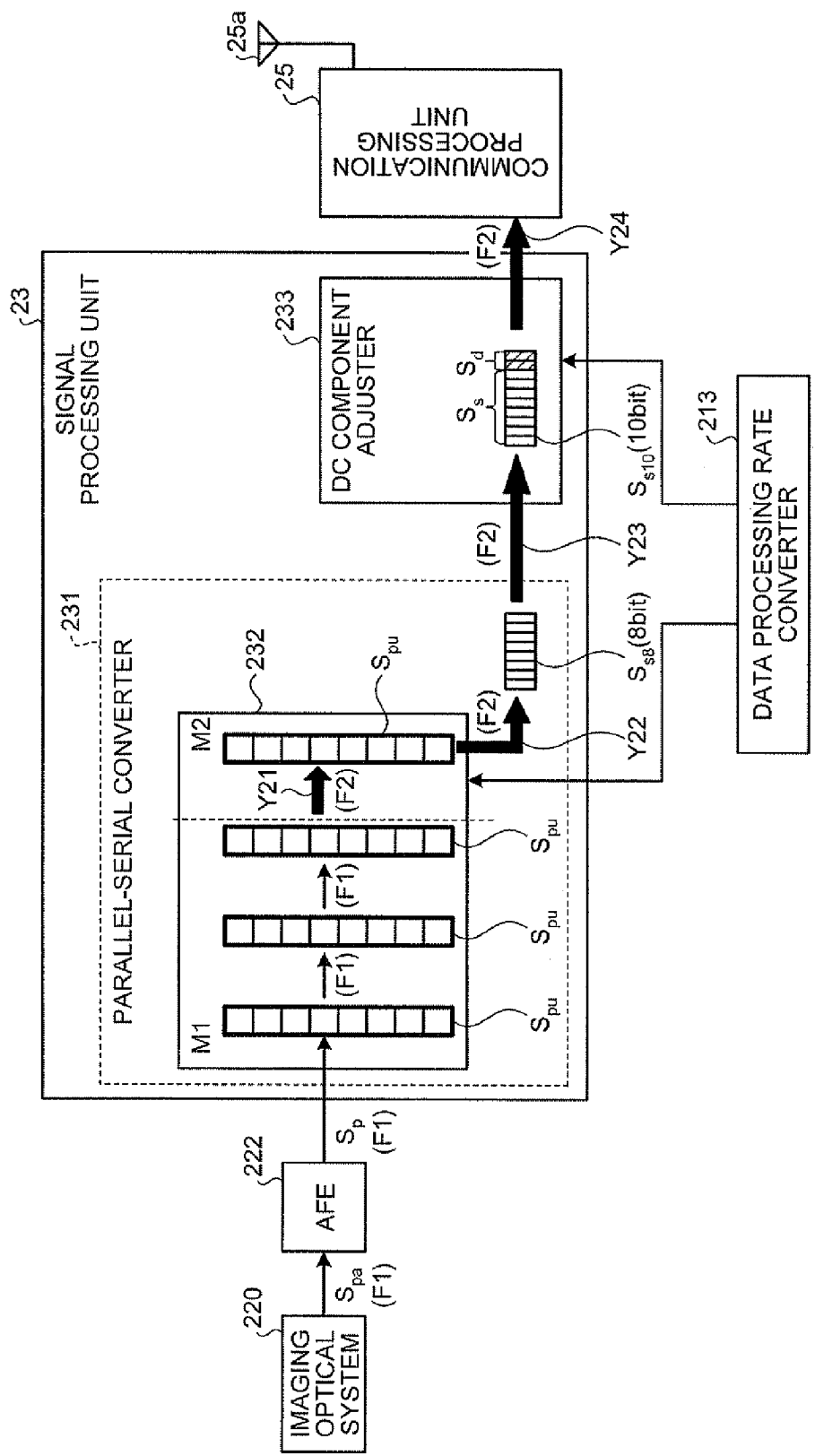
FIG. 3 is a diagram for explaining image data processing performed by the capsule endoscope shown in FIG. 1.

The conversion of the processing rate is explained below. As shown in FIG. 3, the imaging optical system 220 captures the in-vivo image and outputs the image data $S_{pa}$ to the ABE 222 at the processing rate F1. The AFE 222 performs the A/D conversion processing on the data $S_p$ and inputs the image data $S_p$ to the parallel-serial converter 231 also at the processing rate F1 of the imaging optical system 220. The parallel-serial converter 231 writes the image data $S_p$ in a writing area M1 of the memory 232 also at the processing rate F1 at which the AFE 222 inputs the image data $S_p$.

As indicated by an arrow Y21 shown in FIG. 3, the parallel-serial converter 231 sequentially reads the image data $S_p$, which is written in the memory 232 at the processing rate F1, from a reading area M2 by 8-bit pixel data $S_{pu}$.

The parallel-serial converter 231 reads the pixel data $S_{pu}$ from the memory 232 at a transfer processing rate F2 higher than the processing rate F1 at which the image data $S_p$ about the in-vivo image captured by the imaging unit 22 is written in the memory 232. The parallel-serial converter 231 converts the pixel data $S_{pu}$ (8-bit data) read at the transfer rate F2 to 8-bit serial data $S_{s8}$ as indicated by an arrow Y22 shown in FIG. 3, and transfers the serial data $S_{s8}$ (8-bit data) to the DC component adjuster 233 at the transfer rate F2 as indicated by an arrow Y23 shown in FIG. 3.

The DC component adjuster 233 performs 8-10-bit conversion processing at the transfer processing rate F2, in which a 2-bit adjusting signal $S_d$ is added to the serial data $S_{s8}$, thereby obtaining 10-bit serial data $S_{10}$. As indicated by an arrow Y24 shown in FIG. 3, the DC component adjuster 233 transfers the serial data $S_{s10}$ to the communication processing unit 25 at the transfer processing rate F2. The communication processing unit 25 wirelessly transmits the information transferred from the signal processing unit 23 at a transmission rate corresponding to the transfer processing rate F2 of the data processing rate converter 213. Specifically, the communication processing unit 25 wirelessly transmits the serial data $S_{s10}$ via the antenna 25a at, for example, the transfer processing rate F2 as the transmission rate corresponding to the transfer processing rate F2 at which the serial data $S_{s10}$ is input.

In the capsule endoscope 2, under the control by the data processing rate converter 213, the transfer processing rate F2 at which the signal processing unit 23 reads the image data $S_p$ about the in-vivo image captured by the imaging unit 22 from the memory 232 on a pixel basis, converts the image data $S_p$ to the serial data $S_s$, and transfers the serial data $S_s$ is converted to a rate higher than the processing rate F1 at which the image data $S_p$ is written in the memory 232.

In a conventional capsule endoscope, a transfer processing rate at which a signal processing unit reads image data about an in-vivo image captured by an imaging unit from a memory on a pixel basis, converts the image data to serial data, and transfers the serial data is set equal to a writing processing rate at which the image data is written in the memory.

Figure 4:
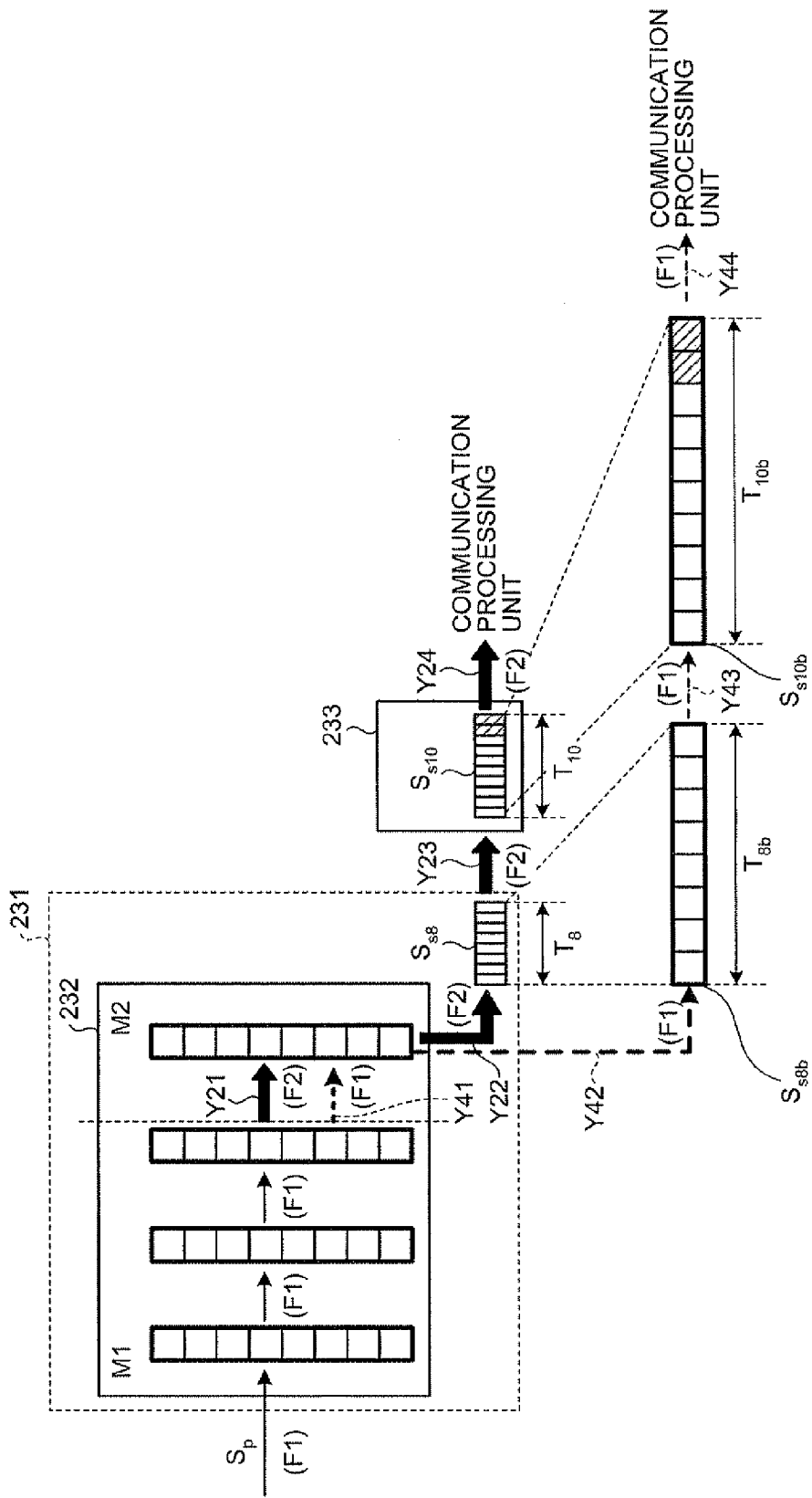
FIG. 4 is a diagram for explaining the image data processing performed by the capsule endoscope shown in FIG. 1.

Specifically, in the conventional capsule endoscope, as indicated by arrows Y41 and Y42 shown in FIG. 4, the image data is sequentially read from a read area of the memory by each pixel data $S_{pu}$ (8-bit data) and the image data is converted to serial data $S_{s8b}$ at the processing rate F1 at which the image data is written in the memory. In the conventional endoscope, at the processing rate F1, the serial data $S_{s8b}$ is transferred to a DC component adjuster that performs the 8-10 bit conversion processing as indicated by an arrow Y43 shown in FIG. 4, the serial data $S_{s8b}$ is converted to serial data $S_{s10b}$, and the serial data $S_{s10b}$ is transferred from the DC component adjuster to a communication processing unit as indicated by an arrow Y44 shown in FIG. 4.

The conventional capsule endoscope performs the image data reading processing, the parallel-serial conversion processing, and the 8-10 bit conversion processing on a bit-by-bit basis on the image data output from the imaging unit and written in the memory by 8 bits. Therefore, to read the image data written by 8 bits form the memory and perform the parallel-serial conversion processing on a bit-by-bit basis at the processing rate F1 at which the image data is written in the memory, a time $T_{8b}$ eight times the time required for writing the image data in the memory is required. Similarly, to perform the 8-10 bit conversion processing on the image data (8-bit data) on a bit-by-bit basis to obtain 10-bit data at the processing rate F1 at which the image data (8-bit data) is written in the memory, a time $T_{10b}$ ten times the time required for writing the image data in the memory is required. Furthermore, because the serial data $S_{s10b}$ is transferred to the communication processing unit only at the processing rate F1, the communication processing unit wirelessly transmits the serial data $S_{s10b}$ at the processing rate F1. In other words, the communication processing unit transmits the image data spending a time ten times the time required for writing the image data in the memory.

Figure 5:
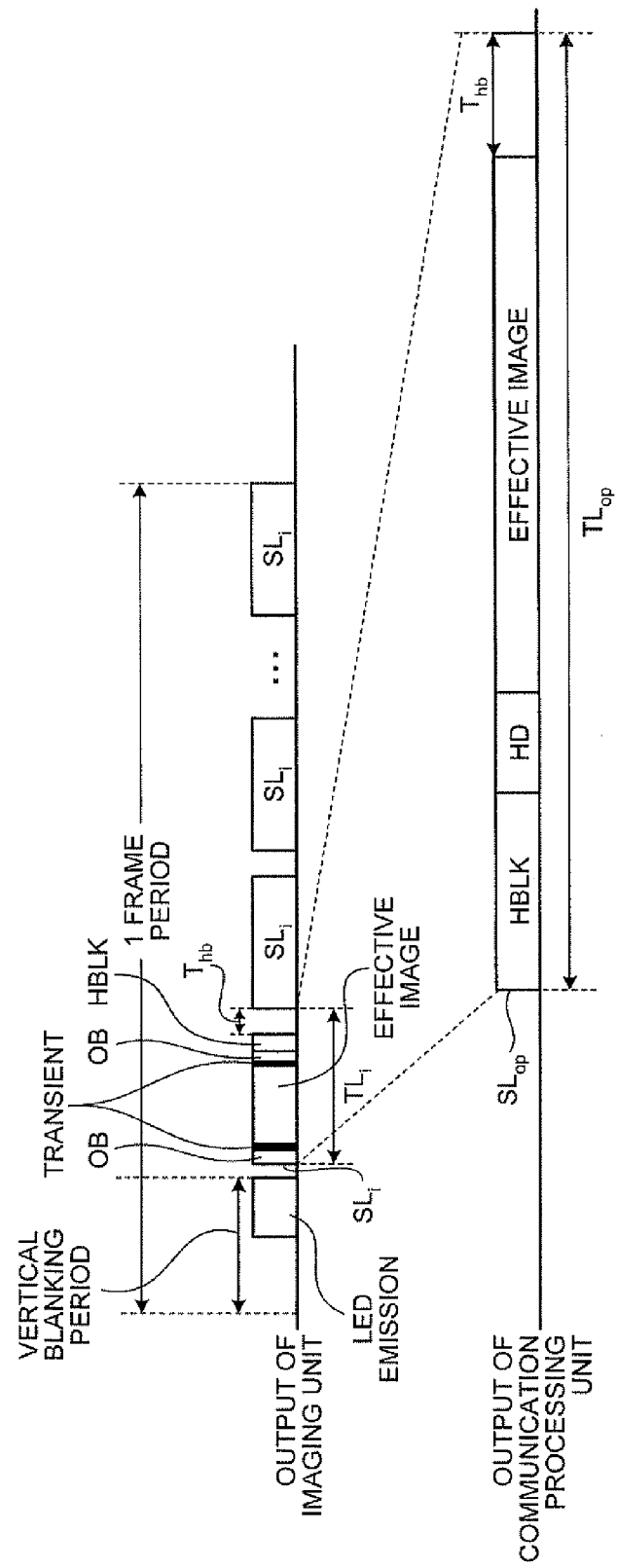
FIG. 5 is a diagram for explaining a time required for transmitting data from a conventional capsule endoscope.

As explained above, in the conventional capsule endoscope, a transmission time $TL_{op}$ ten times an output time $TL_i$ required for outputting the image data from the imaging unit is required to transmit one-line image data $SL_i$ output from the imaging unit as indicated by data $SL_{op}$ shown in FIG. 5. Therefore, in the conventional capsule endoscope, the in-vivo images have to be captured at intervals corresponding to the transmission time ten times the time required for outputting the image data from the imaging unit. In other words, in the conventional capsule endoscope, an imaging waiting time is necessarily caused due to the difference between the transmission processing time and the imaging processing time, which limits an increase in the frame rate.

On the other hand, in the capsule endoscope 2, under the control by the data processing rate converter 213, the transfer processing rate F2 at which the signal processing unit 23 reads the image data $S_p$ acquired by the imaging unit 22 from the memory 232 on a pixel basis, converts the image data to the serial data $S_s$, and transfers the serial data $S_s$ is converted to a rate higher than the writing processing rate F1 at which the image data $S_p$ is written in the memory 232.

Specifically, the parallel-serial converter 231 performs the image data reading processing and the parallel-serial conversion processing on the image data, which is received from the imaging unit 22 and written by 8 bits in the memory 232, on a bit-by-bit basis at the transfer processing rate F2 higher than the processing rate F1 at which the image data is written in the memory 232. Therefore, as shown in FIG. 4, the parallel-serial converter 231 can perform the processing in a time $T_8$ shorter than the time $T_{8b}$ required to perform the processing by the conventional capsule endoscope. In addition, because the DC component adjuster 233 performs the 8-10 bit conversion processing at the transfer processing rate F2 higher than the processing rate F1 at which the image data is written in the memory 232, the DC component adjuster 233 can perform the processing in a time $T_{10}$ shorter than the time $T_{10b}$ required to perform processing by the conventional capsule endoscope. Furthermore, because the serial data $S_{s10}$ to be transmitted is input to the communication processing unit 25 at the transfer processing rate F2 higher than the processing rate F1, the communication processing unit 25 can wirelessly transmits the serial data $S_{s10}$ at the transfer processing rate F2. In other words, the communication processing unit 25 can transmits the image data about the in-vivo image to the outside in the time shorter than the transmission time required by the conventional capsule endoscope.

For example, when the image processing rate of the imaging unit 22 and the processing rate F1 at which the image data is written in the memory 232 correspond to a clock frequency of 2.7 MHz, the data processing rate converter 213 sets the clock frequency corresponding to the transfer processing rate F2 to 27 MHz ten times the clock frequency of the processing rate F1 in accordance with the transmitted 10-bit image data.

In this case, the signal processing unit 23 performs the image data reading processing, the parallel-serial conversion processing, and the 8-10 bit conversion processing on the image data, which is output from the imaging unit 22 and written in the memory 232 by 8 bits, on a bit-by-bit basis at the processing rate 10 times higher than that at which the imaging processing is performed by the imaging unit 22 and the image data is written in the memory 232. The communication processing unit 25 wirelessly transmits the serial data $S_{s10}$ (10-bit data) on a bit-by-bit basis in accordance with the clock frequency of 27 MHz. In other words, the processing for reading the pixel data $S_{pu}$, the parallel-serial conversion processing, the 8-10 bit conversion processing, and the wireless transmission processing, which are performed on a bit-by-bit basis, are performed at the processing rate ten times higher than the imaging processing rate of the imaging unit 22 and the processing rate at which the image data is written in the memory 232.

Figure 6:
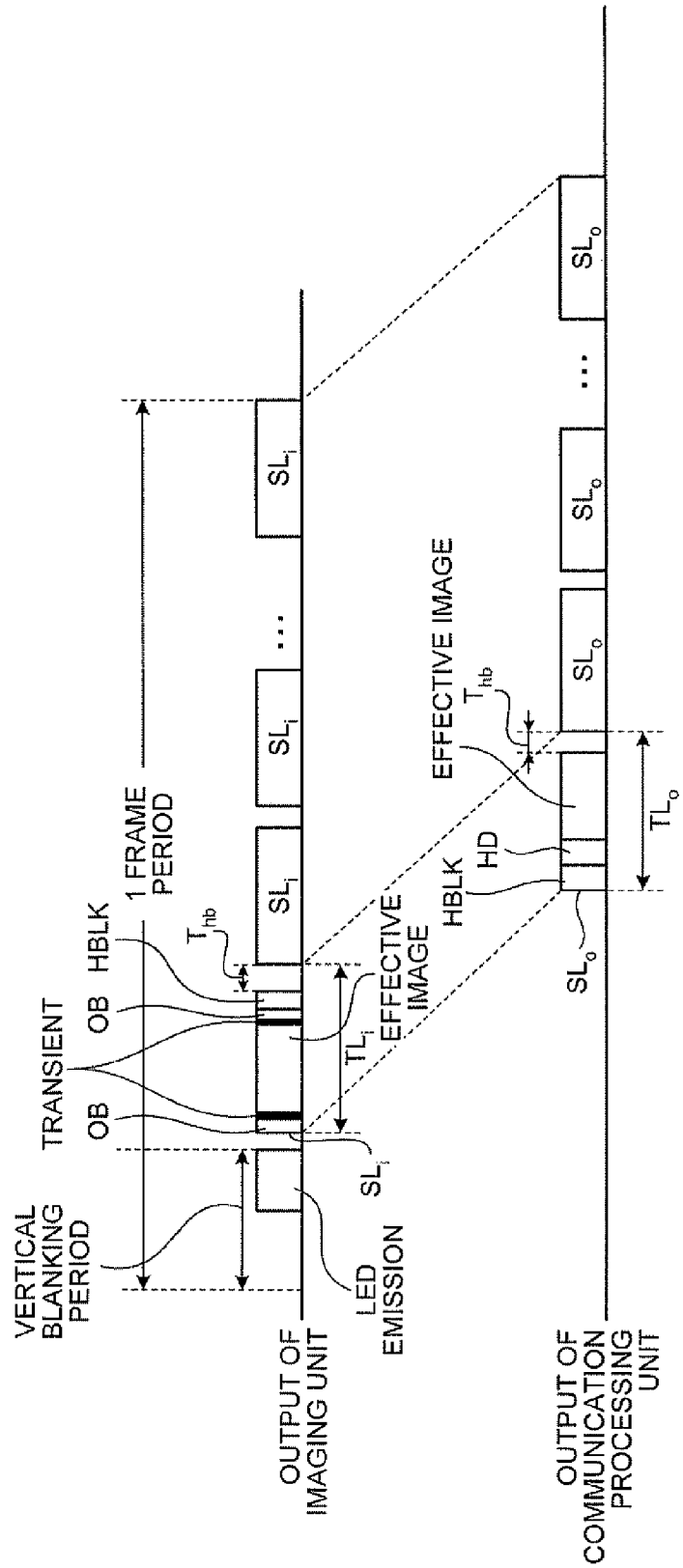
FIG. 6 is a diagram for explaining a time required for transmitting data from the capsule endoscope shown in FIG. 2.

In the capsule endoscope 2, by performing each processing, which is performed on a bit-by-bit basis, ten times faster as explained above, the output time $TL_i$ in which the image data $SL_i$ (8-bit parallel data) is output from the imaging unit 22 can be equal to a transmission time $TL_o$ in which 10-bit serial image data $SL_o$ converted from the image data $SL_i$ is transmitted from the communication processing unit 25 as shown in FIG. 6. In the capsule endoscope 2, by setting the transfer processing rate F2 of the signal processing unit 23 is set to a rate such that the processing time required for the imaging unit 22 to capture each image is equal to the processing time required for the communication processing unit 25 to transmit each image, the imaging wait time due to a difference between the transmission processing time and the imaging processing time can be reduced. This increases the frame rate to the highest rate.

As explained above, in the capsule endoscope 2, by converting the transfer processing rate F2 at which an in-vivo image captured by the imaging unit 22 and temporarily stored in the memory 232 is read on a pixel basis from the memory 232, the in-vivo image is converted to serial data, and the serial data is transferred to a rate higher than the processing rate F1 at which the in-vivo image is written in the memory 232, the time required for wirelessly transmitting the captured in-vivo image to the outside can be shortened. Therefore, the imaging wait time due to a difference between the transmission processing time and the imaging processing time can be reduced. This shortens the intervals at which the imaging unit 22 captures in-vivo images, which increases the frame rate.

Furthermore, in the capsule endoscope 2, the frame rate can be increased by only adding the frequency converter that is relatively a small circuit. Therefore, the circuit is not large-sized compared with a conventional endoscope in which a circuit for image compression is mounted on a control substrate, which prevents the capsule endoscope 2 to be large-sized. Moreover, because the capsule endoscope 2 does not spend a time required for image compression processing, which is necessary in the conventional capsule endoscope, and does not have a load for the image compression processing, the power consumption can be reduced compared with the conventional capsule endoscope in which the circuit for image compression is installed.

The clock frequency of the imaging unit 22 is originally different from the clock frequency of other units. The units other than the imaging unit 22 tends to have a clock frequency higher than that of the imaging unit 22. Therefore, in the capsule endoscope 2, the data processing rate converter 213 can use the clock frequency used for the units other than the imaging unit 22 as the transfer processing rate F2 and the transmission processing rate of the communication processing unit 25. In this case, the capsule endoscope 2 does not require an additional circuit for generating a clock frequency corresponding to the transfer processing rate F2 and the transmission processing rate of the communication processing unit 25.

In the conventional capsule endoscope in which the transfer processing rate and the writing processing rate are equal, the transfer processing performed on a bit-by-bit basis requires a time longer than that required for the writing processing in which an in-vivo image is written in the memory by 8 bits, which results in a large difference between the processing time of the transfer processing and the processing time for the writing processing. Therefore, the conventional capsule endoscope need to have a memory for temporarily storing an in-vivo image with a capacity for at least one in-vivo image as a buffer for the difference between the processing times.

On the other hand, in the capsule endoscope 2, the transfer processing rate F2 at which an in-vivo image captured by the imaging unit 22 is read from the memory 232, the in-vivo image is converted to serial data, and the serial data is transferred is converted to a rate higher than the processing rate F1 at which the in-vivo image is written in the memory 232. Therefore, in the capsule endoscope 2, because the capacity of the memory 232 as a buffer for the difference between the transfer processing time and the writing processing time can be reduced, the circuit configuration can be downsized, which downsizes the capsule endoscope 2.

In the capsule endoscope 2, the transfer processing rate F2 at which the in-vivo image captured by the imaging unit 22 is read from the memory 232, the in-vivo image is converted to serial data, and the serial data is transferred is converted to a rate higher than the processing rate F1 at which the in-vivo image is written in the memory 232. Therefore, in the capsule endoscope 2, the transfer processing time consumed by the signal processing unit 23 can be reduced when the imaging unit 22 employs the same frame rate as that of the conventional capsule endoscope, thereby reducing the power consumption consumed by the signal processing unit 23.

As shown in FIGS. 5 and 6, the image data $SL_i$ (1-line data) output from the imaging unit consists of an OB component, a transient component, an effective image component, and an HBLK component. The top image data $SL_i$ is output from the imaging unit after a vertical blanking period including an LED emission time, and subsequent image data $SL_i$ is output after a horizontal blanking period $T_{hb}$. Each of image data $SL_{op}$ and image data $SL_o$ consists of an HBLK component, an HD synchronization signal, and an effective image component.

Figure 7:
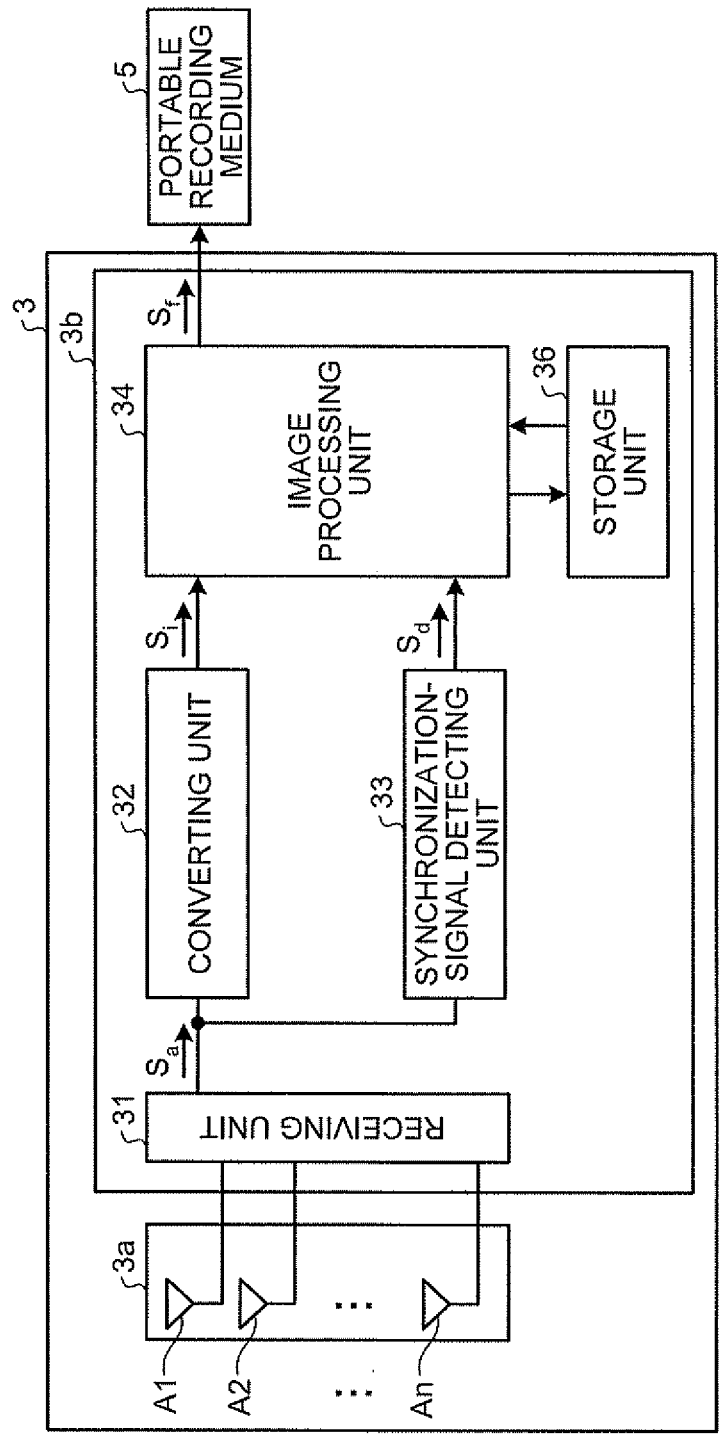
FIG. 7 is a block diagram of a configuration of a receiving apparatus shown in FIG. 1.

The receiving apparatus 3 shown in FIG. 1 is explained below. As shown in FIG. 7, the receiving apparatus 3 includes the wireless unit 3a and the receiving main unit 3b. The receiving main unit 3b includes a receiving unit 31, a converting unit 32, a synchronization-signal detecting unit 33, an image processing unit 34, and a storage unit 36. The receiving unit 31 switches between the antennas A1 to An, and receives a wireless signal via the switched antenna. The receiving unit 31 performs receiving processing including demodulation and analog-digital conversion, and outputs a signal $S_a$. The converting unit 32 converts the signal $S_a$ received from the receiving unit 31 to a signal $S_i$ in a signal format processable by the image processing unit 34. The converting unit 32 outputs the signal $S_i$ in synchronization with synchronization signal output timing of the synchronization-signal detecting unit 33. The synchronization-signal detecting unit 33 detects various types of synchronization signals from the signal $S_a$, and outputs a synchronization signal information $S_d$ about the detected synchronization signals to the image processing unit 34. The image processing unit 34 performs predetermined processing on the signal $S_i$ received from the converting unit 32, and outputs image data $S_f$ corresponding to an image of one frame. The storage unit 36 stores therein information necessary for image processing performed by the receiving apparatus 3.

Because the time required for the capsule endoscope 2 to transmit a wireless signal is shortened compared with the conventional capsule endoscope as explained above, the time for the receiving apparatus 3 to receive the wireless signal from the capsule endoscope 2 is shortened, which shortens the processing time until the image data $S_f$ is output. Accordingly, in-vivo images can be supplied fast compared with the conventional capsule endoscope.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A body-insertable apparatus comprising:
   an imaging unit that captures an in-vivo image of a subject;
   a signal processing unit that includes a memory in which the in-vivo image is temporarily stored, writes the in-vivo image in the memory, the signal processing unit reading the in-vivo image from the memory on a pixel basis and converting the in-vivo image to serial information to transfer the serial information;
   a rate converter that converts a transfer processing rate to a rate higher than a writing processing rate, the transfer processing rate being at which the signal processing unit reads the in-vivo image from the memory and converts the in-vivo image to the serial information to transfer the serial information, the writing processing rate being at which the signal processing unit writes the in-vivo image in the memory; and
   a transmitting unit that wirelessly transmits the serial information transferred from the signal processing unit at a transmission rate corresponding to the transfer processing rate.

2. The body-insertable apparatus according to claim 1, wherein the rate converter increases the transfer processing rate by increasing a clock rate to be supplied to the signal processing unit.

3. The body-insertable apparatus according to claim 1, wherein the rate converter sets the transfer processing rate such that an imaging processing time required for the imaging unit to capture an in-vivo image is equal to a transmission processing time required for the transmitting unit to transmit an in-vivo image.

4. An in-vivo information acquiring system comprising:
   a body-insertable apparatus that is introduced into a subject, and transmits a wireless signal including an in-vivo image of the subject to the outside of the subject; and
   a receiving apparatus that receives the wireless signal received from the body-insertable apparatus,
   wherein the body insertable apparatus includes
   an imaging unit that captures an in-vivo image of a subject;
   a signal processing unit that includes a memory in which the in-vivo image is temporarily stored, writes the in-vivo image in the memory, the signal processing unit reading the in-vivo image from the memory on a pixel basis and converting the in-vivo image to serial information to transfer the serial information;
   a rate converter that converts a transfer processing rate to a rate higher than a writing processing rate, the transfer processing rate being at which the signal processing unit reads the in-vivo image from the memory and converts the in-vivo image to the serial information to transfer the serial information, the writing processing rate being at which the signal processing unit writes the in-vivo image in the memory; and
   a transmitting unit that wirelessly transmits the serial information transferred from the signal processing unit at a transmission rate corresponding to the transfer processing rate.

5. The in-vivo information acquiring system according to claim 4, wherein the rate converter increases the transfer processing rate by increasing a clock rate to be supplied to the signal processing unit.

6. The in-vivo information acquiring system according to claim 4, wherein the rate converter sets the transfer processing rate such that an imaging processing time required for the imaging unit to capture an in-vivo image is equal to a transmission processing time required for the transmitting unit to transmit an in-vivo image.

* * * * *